(12) United States Patent
Mikami

(10) Patent No.: US 6,945,966 B2
(45) Date of Patent: Sep. 20, 2005

(54) ABSORBENT BREAST PAD

(75) Inventor: Ikuko Mikami, Tokyo (JP)

(73) Assignee: Pigeon Corporation, Tokyo (JP)

( * ) Notice: Subject to any disclaimer, the term of this patent is extended or adjusted under 35 U.S.C. 154(b) by 89 days.

(21) Appl. No.: 09/763,882

(22) PCT Filed: Jun. 22, 2000

(86) PCT No.: PCT/JP00/04094

§ 371 (c)(1),
(2), (4) Date: Nov. 21, 2002

(87) PCT Pub. No.: WO01/00051

PCT Pub. Date: Jan. 4, 2001

(65) Prior Publication Data

US 2004/0225268 A1 Nov. 11, 2004

(30) Foreign Application Priority Data

Jun. 30, 1999 (JP) .......................................... 11-186469
Jun. 30, 1999 (JP) .......................................... 11-186470

(51) Int. Cl.$^7$ ............................ A61F 5/44; A61F 13/20; A61F 13/15; A41C 3/00
(52) U.S. Cl. .................. 604/346; 604/355; 604/385.07; 604/387; 450/37
(58) Field of Search .......................... 604/327, 346, 604/355, 385.01, 385.07, 385.24, 387, 388; 128/890; 602/41; 2/267; 450/37, 57

(56) References Cited

U.S. PATENT DOCUMENTS

| | | | | |
|---|---|---|---|---|
| 2,748,771 A | * | 6/1956 | Richards | 604/346 |
| 3,513,852 A | * | 5/1970 | Seidl | 450/36 |
| 4,125,114 A | * | 11/1978 | Repke | 604/366 |
| 4,193,404 A | * | 3/1980 | Repke et al. | 604/366 |
| 4,338,946 A | * | 7/1982 | Donnelly | 450/57 |
| 4,674,510 A | * | 6/1987 | Sneider | 450/57 |
| 4,787,381 A | * | 11/1988 | Hubbard et al. | 602/44 |
| 5,017,174 A | * | 5/1991 | Gowrylow | 450/37 |
| 5,149,336 A | * | 9/1992 | Clarke et al. | 604/388 |
| 5,683,286 A | * | 11/1997 | Kielland | 450/37 |
| 5,690,536 A | * | 11/1997 | Madden et al. | 450/37 |
| 5,858,014 A | * | 1/1999 | Kepes et al. | 604/387 |
| 5,931,717 A | * | 8/1999 | Lidji | 450/37 |
| 6,036,577 A | * | 3/2000 | Coburn | 450/57 |
| 6,074,273 A | * | 6/2000 | Turner et al. | 450/37 |
| 6,159,190 A | * | 12/2000 | Tanaka et al. | 604/385.24 |
| 6,241,715 B1 | * | 6/2001 | Houser et al. | 604/385.07 |
| 6,364,741 B1 | * | 4/2002 | Ferguson | 450/57 |
| 2003/0163071 A1 | * | 8/2003 | Cominsky | 602/41 |

FOREIGN PATENT DOCUMENTS

| | | | | |
|---|---|---|---|---|
| EP | 1 125 511 A1 | * | 8/2001 | ............ A41C/3/04 |
| JP | U-H1-83005 | | 6/1989 | |
| JP | A-H4-209802 | | 7/1992 | |
| JP | U-H6-33911 | | 5/1994 | |
| JP | A-2000-178805 | | 6/2000 | |
| WO | WO 00/09056 | * | 2/2000 | ............ A61F/13/15 |

* cited by examiner

Primary Examiner—Larry I. Schwartz
Assistant Examiner—M G. Bogart
(74) Attorney, Agent, or Firm—Westerman, Hattori, Daniels & Adrian, LLP

(57) ABSTRACT

An object of the present invention is to provide a breast pad which avoids discomfort caused by thermal deformations and heat treatments. In considering this, the breast pad of the present invention has a maim body formed by laminating and fixing together a liquid-absorbing member 12, a waterproof member 11 disposed at an outside of the liquid-absorbing member and a surface member 13 disposed on a surface of the liquid-absorbing member opposite to a surface on which the waterproof member is disposed. The main body further includes elastic members 17, 17 each disposed on a respective side edge portion of the main body, and side edges 13a of the surface members to be disposed at a user's skin side are folded so as to embrace side edges of the liquid-absorbing member therein.

10 Claims, 7 Drawing Sheets

F I G. 8
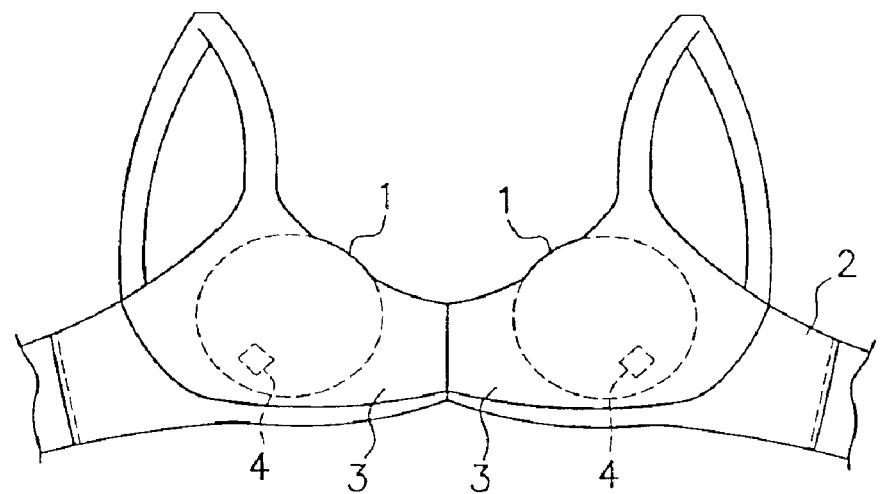
F I G. 9
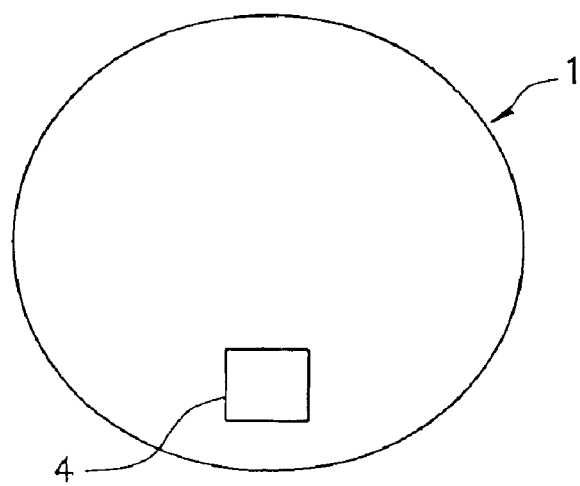

ABSORBENT BREAST PAD

TECHNICAL FIELD

The present invention relates to an improved breast pad for a nursing mother which is to be placed between underwear such as a brassiere and a breast.

BACKGROUND INFORMATION

The type of breast pad which has been conventionally used is shown in FIG. 8. In this drawing, each of the breast pads 1, which is in an approximately circular dome shape, is placed in each cup 3 of a brassiere 2.

The breast pad 1, as shown in a front view in FIG. 9 and in a side view in FIG. 10, is of a circular dome shape and is comprised of a plurality of flexible members laminated in the thickness direction. In detail, the breast pad 1 is made by laminating a surface member disposed on an inner surface which directly touches a user's skin, an absorbent member and a waterproof member for preventing fluid from leaking from the absorbent member to clothing.

An adhesive member 4 is formed at a predetermined position on the surface of the waterproof member. As shown in FIG. 8, the adhesive member 4 is adhered to an inner surface of the cup 3 of the brassiere 2 to fix the breast pad. In this manner, these breast pads 1 are prevented from slipping off the underwear.

In the meantime, the breast pad 1 is formed into a dome shape as mentioned above so as to closely cover a breast of a user(not shown).

In order to manufacture the breast pad 1 of such a shape, a method shown in FIG. 11 has been conventionally employed.

As shown in FIG. 11, members constituting the main body of the breast pad 1 are laminated as explained above, and then placed onto a female die 5 having a bowl-shaped inner surface. Thereafter, a male die 6 having a convex dome shape as shown in FIG. 11 is lowered to press the members while heating the members by the male die 6 and/or female die 5.

In this manner, the heated main body of the breast pad 1 is formed into a dome shape.

Since it is necessary to deform the members into a dome shape with heat in the manufacturing process, the waterproof member of the breast pad 1, for example, is made of a heat-deformable materials such as a polyethylene laminate sheet.

Consequently, the breast pad 1 as a final product has relatively hard feeling after the heat deformation, and is not necessarily comfortable as a final product for directly touching a user's skin.

In some breast pads 1, various considerations are taken such as the surface member (to be directly fitted to a user's skin) is softened and a special processing is applied to the sealed portion between the surface member and the waterproof member, so as not to cause an unpleasant feeling via the peripheral edge of the round pad. However, in cases where the whole waterproof member is thermally deformed, such a partial improvement did not help to avoid the hard feeling of the product. Accordingly, it was difficult to obtain a conformable product.

In addition, even if the main body of the breast pad 1 is formed to have a dome-shape by the heat deformation process, the main body is poor in shape-retaining ability, resulting in a flat shape during wearing. This in turn causes the shape of the breast pad to be inconsistent with the front shape of the user's breast, deteriorating the fitting of the breast pad, which causes the slipping of the breast pad. A resulting drawback is that breast milk is spilled without being absorbed thus soiling the user's clothing.

The present invention is proposed to solve the aforementioned problems. The first object thereof is to provide a breast pad which can be formed to have a dome-shape and is excellent in shape-retaining performance.

In addition, the second object of the present invention is to provide a dome-shaped breast pad which has not been formed by a heat treatment process, so as to avoid discomfort associated with materials which have been subjected to heat deformation and/or heat treatment.

DISCLOSURE OF THE INVENTION

The first object of the present invention according to claim 1 can be attained by a breast pad having a main body formed by laminating a waterproof member on an outside of a liquid-absorbing member, characterized in that the main body is provided with elastic members each disposed at a respective side edge portion of the main body and concave grooves each provided inside each of the elastic members and extended in an expansion direction of each of the elastic members.

According the structure of the claim 1, since the elastic members are disposed at the side edge portions of the main body, the length of the peripheral edge portion of the main body provided with the elastic member becomes shorter because the peripheral edge portion is drawn together in the direction of the elastic member. This causes the central portion of the main body to be protruded in one direction, resulting in a dome-shape corresponding to the front shape of a user's breast.

In particular, concave grooves are each provided inside the elastic members so as to extend in an expansion direction of each of the elastic members, so that the peripheral edge portion of the main body is folded at a folding potion where the concave groove is disposed. Consequently, the main body becomes a more perfect three-dimensional dome shape, and has a superior shape-retaining ability.

Accordingly, a breast pad fitting a breast shape can be produced without heat treatment.

The shape of the main body which becomes dome-shaped by providing an elastic member at the peripheral edge portion thereof, is typically round in shape. However, the shape is not limited to a perfectly round shape, and may be of any shape in which the vertical-horizontal length ratio is not large. For example, the main body may be a square shape, a trapezoid shape or the like having rounded corners and have relatively large (long) elastic members disposed at each peripheral side by which the length of each peripheral side becomes shorter due to the elasticity of the elastic members, thus becoming dome-shaped.

The aforementioned term, "dome shape" or "dome shaped," denotes any shape having a convex cross-section and a hemispherical shape when cut so as to cross the center thereof.

According to the present invention of claim 2 depending from claim 1, the concave groove curves along the expansion direction of the elastic member.

With this structure, since a folding portion is curved, the folding portion becomes in a curved and bent state which is more suitable for forming a dome-shaped breast pad.

According to the present invention of claim 3, the concave groove curves so as to protrude toward a central portion of the main body along the expansion direction of the elastic member.

With the structure of claim 3, an ideal conical dome shape can be produced in which a sectional area decreases toward the central portion.

According to the present invention of claim 4 depending from any one of claims 1 to 3, a surface member which comes in contact with a user's skin is disposed on a surface of the liquid-absorbing member opposite to a surface on which the waterproof member is disposed, and a cushion member is disposed between the liquid-absorbing member and the surface member.

With the structure of claim 4, since the surface member comes in contact with a user's breast because of the action of the cushion member, it is difficult for the breast pad to slip out of its location.

According to the present invention of claim 5 depending from claim 4, a surface member is provided with the concave grooves at both side portions of a nipple-contact portion of the surface member.

With the structure of claim 5, since the surface member and the liquid-absorbing member disposed under the surface member are fixed to each other at the grooves, members disposed in the main body are hard to be displaced. Furthermore, since both the side portions of the nipple contact portion are dented by the grooves, a space for accommodating a nipple is formed and the nipple contact portion rises to come in soft contact with the nipple.

The second object of the present invention can be attained by claim 6. According to the present invention of claim 6, a breast pad has a main body formed by laminating and adhering together a liquid-absorbing member, a waterproof member disposed at an outside of the liquid-absorbing member and a surface member disposed on a surface of the liquid-absorbing member opposite to a surface on which the waterproof member is disposed.

With the structure of claim 6, since the elastic members are disposed at each respective side edge portion of the main body, the peripheral edge portion of the main body becomes shorter at the portion where the elastic members are disposed by being pulled in a direction in which the elastic members are disposed. Accordingly, the central portion of the main body protrudes toward one side, so that the main body becomes dome-shaped so as to accommodate a front shape of a breast.

Accordingly, the breast pad fitting a breast can be produced without thermally deforming the materials. In this manner, no materials hardened by heat are produced, so that unpleasant feelings caused by the contact of the user's skin with hardened materials, can be avoided.

Here, the main body of the breast pad can be formed to have a dome-shape by the action of elastic members without heat deformation. However, wrinkles will be produced when the elastic members are shrunk if there are materials fixed to the elastic members. In this case, the hardened wrinkles may cause unpleasant feelings when they contact the user's skin.

Accordingly, in the structure of the above-mentioned claim 6, the side edge portions of the surface member to be disposed at a user's skin side are folded so as to embrace side edges of the liquid-absorbing member therein. With this structure, since the side edges of the breast pad are covered by relatively soft materials, a user will not experience discomfort even if the relatively soft materials come in contact with a user's skin.

In this case, the surface member may embrace only the side edge portion of the liquid-absorbing member, alternatively may embrace the side edge portion of the liquid-absorbing member together with the elastic member.

According to the present invention of claim 7 depending from claim 6, the edge portion of the surface member is folded so as to embrace the liquid-absorbing member and the elastic member therein at a side edge of the main body.

With the structure of claim 7, since the surface member embraces the elastic member as well as the liquid-absorbing member in the region where the elastic member is disposed on the edge of the main body, the function according to claim 6 can be more fulfilled.

According to the present invention of claim 8 depending from claim 6 or 7, the elastic member is fixed to the liquid-absorbing member and the folded surface member, or to the folded surface member and the waterproof member, in a state in which the elastic member is sandwiched therebetween at a side edge of the main body, and both longitudinal opposite ends of the elastic member have portions not fixed to the main body.

With the structure of claim 8, since the edge of the long elastic member has a free portion not fixed to the main body of a breast pad, especially the peripheral edge portion of the main body, the peripheral edge portion is not pulled inwardly. This prevents an inward bending of the peripheral edge portion of the main body. Accordingly, such an inwardly bent portion does not give uncomfortable stimulation to a user because it does not come into contact with a user's skin.

According to the present invention of claim 9 depending from claim 8, the liquid-absorbing member is formed to be smaller than the waterproof member and the surface member at a region in which the opposite end'portions of the elastic member are disposed, and opposite end portions of the elastic member have portions not fixed to the waterproof member and the surface member.

With the structure of claim 9, in addition to the function of claim 8, the liquid-absorbing member is smaller than the waterproof member, and therefore, the material cost can be reduced.

According to the invention of claim 10 depending from any one of claims 6 to 9, at an approximately expanding center of the elastic member on side edge portions of the main body, the waterproof member has an area not fixed to the liquid-absorbing member and/or the surface member.

With the structure of claim 10, at the portion where the elastic member is disposed, the waterproof member can avoid being turned inwardly due to being pulled by the elastic member.

BRIEF DESCRIPTION OF THE DRAWINGS

FIG. 8 is an explanatory view of a conventional breast pad.

FIG. 9 is a front view of the breast pad of FIG. 5.

PREFERRED EMBODIMENTS OF THE INVENTION

A preferred embodiment of the present invention will be described in detail with reference to the attached drawings.

Although the preferred embodiments described below includes technically preferable limitations, the scope of the present invention is not limited to these embodiments so long as there is no specific description such that the present invention is limited to it.

Figure 1:
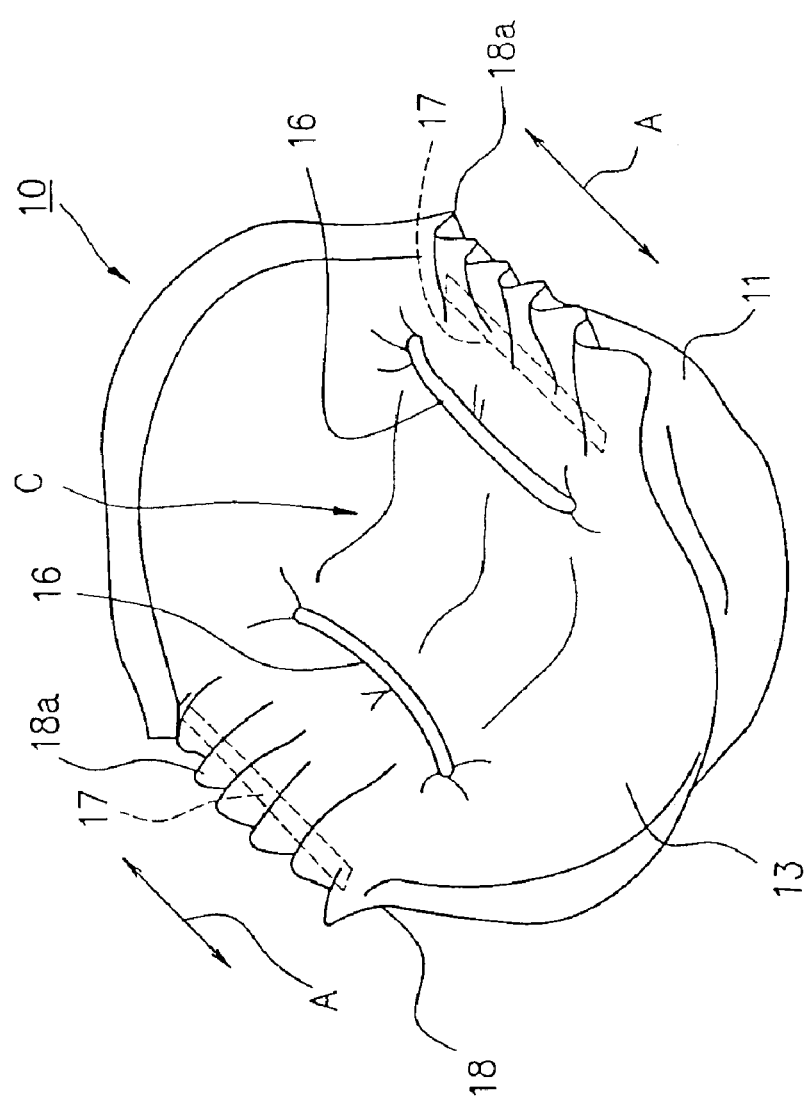
FIG. 1 is a schematic perspective view of an embodiment of a breast pad according to the present invention.
Figure 2:
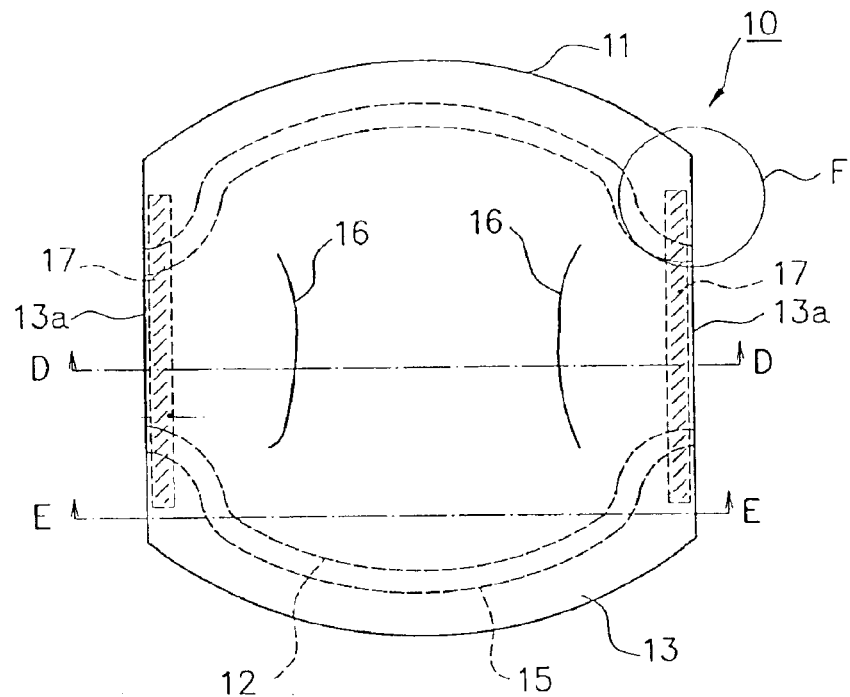
FIG. 2 is a schematic plan view with the inner side of the breast pad facing up.
Figure 3:
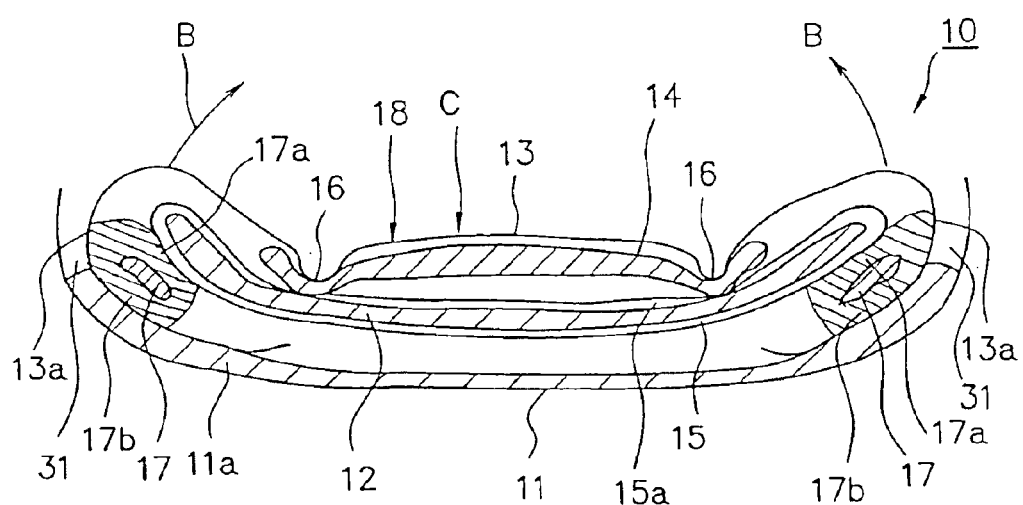
FIG. 3 is a schematic cross-sectional view taken along the line D—D of FIG. 2.
Figure 4:
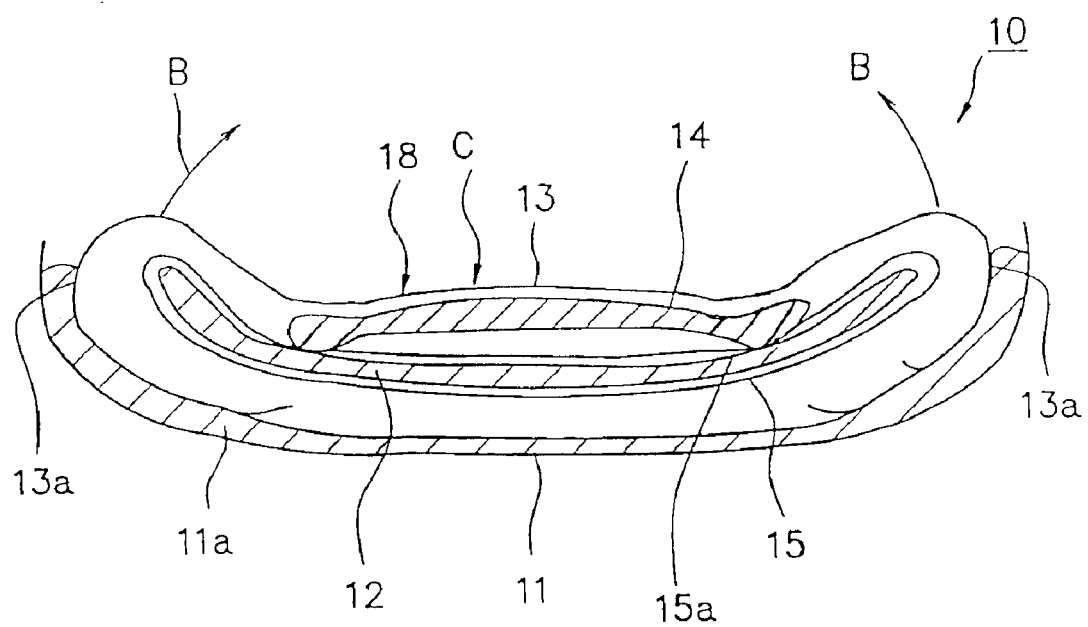
FIG. 4 is a schematic cross-sectional view taken along the line E—E of FIG. 2.

FIG. 1 is a schematic perspective view seen from the inner side of the breast pad according to an embodiment of the present invention. FIG. 2 is a plan view with the inner side of the breast pad facing up. FIG. 3 is a cross-sectional view taken along the line D—D of FIG. 2. FIG. 4 is a cross-sectional view taken along the line E—E of FIG. 2.

The structure of the present embodiment will now be explained with reference to these drawings.

A waterproof member 11 is disposed on the outer surface (equivalent to the lower side of FIG. 1) of the breast pad 10, and a surface member 13 is disposed on the inner surface (equivalent to the upper side of FIG. 1) to be contacted to a user's skin when wearing the breast pad 10.

As shown in FIGS. 3 and 4, a liquid-absorbing member 12 is disposed between the surface member 13 and the waterproof member 11, and a cushion member 14 is disposed between the liquid-absorbing member 12 and the surface member 13.

The external configuration of the waterproof member 11 that gives shape to the main body 18 of the breast pad 10 and the surface member 13, is approximately round, and the sides thereof are formed to be straight.

The above-mentioned waterproof member 11 is a backsheet and is fixed to the upper side member shown in FIG. 3 by applying adhesive on a portion of an adhering part 11a. Although the waterproof member 11 does not allow water to pass through, it is preferably made of materials which allow vapor to pass through to thereby prevent getting musty and has a certain level of flexibility. The waterproof member 11 is comprised of softer materials compared with conventional thermally deformable waterproof members. Examples of such materials include polyethylene film, polyethylene lamination nonwoven fabric, nonwoven fabric produced by a method of meltblowing and the like.

The above-mentioned surface member 13 is a member to be contacted directly to the user's skin. Accordingly, such materials should be selected from materials allowing fluid such as breast milk to pass through and giving pleasant feelings. That is, since the surface member 13 is to be directly contacted to the user's skin, the materials of the surface member should be selected from appropriate materials having pleasant feelings to a skin. Examples of such materials include a dry-mesh sheet (mesh sheet formed of the polyethylene and the like) and a nonwoven fabric. The surface member 13 is disposed so as to involve the liquid-absorbing member 12 mentioned below, and the elastic member 17 by holding the extended side edges 13a, preferably the extended whole peripheral edge, toward the front side.

In this manner, even if the elastic member 17 produces wrinkles facing inwardly as shown in FIG. 1 by the elasticity and they come in contact with a user's skin, they do not give unpleasant feelings or stimulus because they are covered by soft materials.

As will be understood from the comparison of FIGS. 3 and 4, non-bonding portions 31, 31 in which the waterproof member 11 is not bonded to the side edge potions 13a, 13a of the folded surface member 13 is provided at the central portion (around the line D—D in FIG. 2) of the main body 18. Because of this, when the elastic member 17 mentioned below, acts and the edges thereof are pulled toward a user's skin, the waterproof member 11 does not follow them. In this manner, unpleasant feelings can be avoided even when the waterproof member 11 comprised of harder materials as compared to the surface member 13 comes in contact with a user's skin.

The liquid-absorbing member 12 is made of materials having liquid absorbing ability, for example, a pulp-fabric, a pulp-lamination or a sheet member and the like. It is preferable that the liquid-absorbing member 12 is a mixture of pulp materials in which grain-like polymers are mixed, wherein the grain-like polymers are superior in liquid-absorbing ability and can retain liquid by semi-congealing or congealing.

As the materials, for example, absorbent copolymer, e.g., polyacrylic acid-base copolymer, hydrolysis of starch-acrylonitrile graft copolymer, starch-acryl acid graft copolymer, polyvinyl alcohol-acrylate copolymer, carboxymethyl cellulose and the like, is appropriately used.

As shown in FIGS. 3 and 4, the liquid-absorbing member 12, is embraced by a tissue 15 so as not to allow materials such as grain-like polymer to be leaked.

As shown in FIG. 3, the edge 15a of the tissue 15 surrounding the liquid-absorbing member 12 is fixed at the portion apart from the center of the main body 18.

The cushion member 14 disposed between the liquid-absorbing member 12 and the surface member 13 is formed of, for example, a hydrophilic nonwoven fabric having a certain thickness to have a soft swelling.

In this embodiment, the cushion member 14 is formed to be smaller than the main body 18 and placed only in the center of the main body 18.

Furthermore, as shown in FIGS. 1 and 2, the surface member 13 is provided with concave grooves 16 formed on both sides of the nipple contact region C along the direction of an arrow A, or the longitudinal direction of the elastic member 17.

As shown in FIG. 3, the concave groove 16 is formed by an embossing method and the like, pressing while applying a prescribed pressure onto the main surface of the surface member 13, preferably pressing into the cushion member 14. Consequently, since the surface member 13 and the cushion member 14, disposed under the surface member, are fixed at this groove, the surface member 16, the liquid-absorbing member 12 and the cushion member 14, which constitute the main body 18, are not easily displaced from each other.

Each concave groove 16 may have uneven portions formed by changing the depth to the main body 18. Thus, an embossed uneven groove along the expansion direction of the groove is formed, resulting in an enhanced bonding strength, which in turn increases the shape-holding strength of the main body 18.

As shown in FIG. 3, each concave groove 16 acts as a folding portion so as to bend the peripheral edge of the main body 18 in the direction of an arrow B. This forms a three-dimensional dome-shape with the effect of an elastic member 17 which will be mentioned later.

In this manner, the whole central portion C of the main body 18 becomes a concave portion forming a nipple accommodating space, which prevents the user's nipple from being unnecessary pressured. Additionally, the central portion of the aforementioned region C slightly swells in the thickness direction, resulting in a soft fit to the nipple.

In the cross-sectional view in FIGS. 3 and 4, the thickness of the breast pad is shown exaggeratedly such that it appears considerably thicker than that of a real breast pad for an easy explanation of the inner structure.

Additionally, in the breast pad 10, the elastic members 17, 17 are disposed on both sides of the main body 18. In this embodiment, these elastic member 17 are disposed approximately in parallel along a vertical direction (see FIG. 1 or FIG. 2) of the product and have a specific length. In this case, as shown in FIG. 3, each elastic member 17 is fixed to the liquid-absorbing member 12 at an adhering portion 17a via the tissue 15, and further at the adhering portion 17b in a state that the periphery is embraced by at least side end portion 13a, preferably by the whole periphery.

The materials affected by the elastic action of the elastic member 17 are comprised of the soft surface member 13 or the liquid-absorbing member 12. This elastic action does not affect the waterproof member 11 because the elastic member 17 is not fixed to the waterproof member 11.

Accordingly, the waterproof member 11, giving hard feelings as compared to the surface member 13, does not produce wrinkles at the peripheral edge portions 18a, 18a of the main body 18 where both elastic members 17 are disposed. Thus, wrinkles' are produced in a member other than the waterproof material 11, especially in the surface member 13 made of nonwoven fabric or the like.

Consequently, as will be mentioned later, uncomfortable feelings will not be given to the user even in cases where hard wrinkles comes in contact with the sensitive skin around the user's nipple.

In order to obtain approximately the same effects as mentioned above, the side edge portion 13a of the surface member may embrace not both the liquid-absorbing member 12 and the elastic material 17 but only the liquid-absorbing member 12. In this case, by disposing the elastic member 17 inwardly from the edge, the surface member 13 and the liquid-absorbing member 12 are disposed between the user's skin and wrinkles of the waterproof member 11, so that the user's skin is not directly contacted by the surface member 13 and the liquid-absorbing member 12.

As for the above-mentioned elastic member 17, various forms of members/materials can be used so long as it is made of elastic materials which can expand and contract in its longitudinal direction and can shorten the edge portion of the main body 18 where the elastic member is disposed.

In this embodiment, the elastic member 17, 17, being flexible in one direction and made of soft materials, is preferably used. In other words, the elastic member 17 may be made of, for example, a long natural rubber member, an expandable-and-contractible film, an operon tape, a combination thereof or a mixture/combination of a regular fabric and an expandable-and-contractible fabric.

Due to the function of the elastic member 17, since a part of the circumference of the approximately round-shaped main body 18 is elastically pulled, the entire circumference thereof becomes shorter. This causes the central portion of the main body 18 to protrude toward one side, resulting in a dome-shaped or a cup-shaped main body 18.

The elastic member 17 is preferably disposed below (lower side in FIG. 3) the cushion member 14 because of the following reasons. Even if the surface member 13 is disposed between the cushion member 14 and the elastic member 17, disposing the elastic member 17 near a user's skin deteriorates comfortable and pleasant feelings.

Furthermore, if the elastic member 17 is disposed too close to the surface member 13, the function for properly shortening the edge of the peripheral edge portion due to the elasticity of the elastic member 17 cannot sometimes be obtained. Accordingly, as mentioned above, the elastic member 17 is preferably fixed to the liquid-absorbing member 12 at the peripheral edge of the main body 18.

Regarding the tissue 15 embracing the liquid-absorbing member 12 as mentioned above, the joint portion of the tissue 15a should not be located at the center of liquid-absorbing member 12, but be located at a portion closer to the edge thereof, for example, at the portion shown in the drawings. Thus, the joint portion does not come into contact with the user's nipple, thereby preventing uncomfortable feelings on the user's sensitive nipple. Furthermore, since the joint portion 15a is not located at the nipple-contact portion, the adhesive used on the joint portion 15a will not prevent the absorption of the mother's milk coming from a nipple.

The elastic function of the elastic member 17 acts on the peripheral edge portion of the main body 18 and the main body 18 is bent along the above-mentioned concave groove 16. This causes the main body 18 to be a three-dimensional dome shape with the central region C protruding.

The concave groove 16 is preferably formed in a curved shape, which results in a more dome-like shape of the main body 18.

For example, as shown in FIG. 2, the central portion 16a of each respective concave groove 16 is formed to be a curved shape protruding toward the central portion of the main body 18, which forms an approximate ideal conical dome shape with the region C whose sectional area decreasing toward the central portion.

Alternatively, the curved shape of each respective concave groove 16 may, in contrast to FIG. 2, protrude toward the outer periphery of the main body 18. In this case, the dome shape formed by the curved portion of the concave groove 16 will be a larger-sized dome shape with the inward region C having a larger area (capacity).

The surface of the waterproof member 11 of the breast pad 10 may be provided with an adhering portion as shown in FIG. 9.

In the breast pad 10 according to the present embodiment, the upper half portion and the lower half portion are symmetrically formed as shown in FIG. 2, and the elastic member 17 is not disposed at the upper or lower side of the main body 18. In other words, the elastic member 17 is disposed along the respective lateral edges of the main body 18, and the upper and lower edges thereof extend beyond the area where the liquid-absorbing member 12 is disposed, which will be understood from the comparison of FIGS. 3 and 4.

Since four corners of the breast pad 10 in the present embodiment are the same in structure, the structure will be explained with reference to FIG. 5, the enlarged area surrounded by the reference letter F in FIG. 2.

The breast pad 10 has an approximately round shaped main body 18 and is provided with elastic members 17 at both sides of the main body 18, and both sides thereof are formed to be straight. In this manner, as shown in FIG. 5, a corner 32 is formed at an upper portion where the round peripheral edge and the straight side edge cross.

Figure 5:
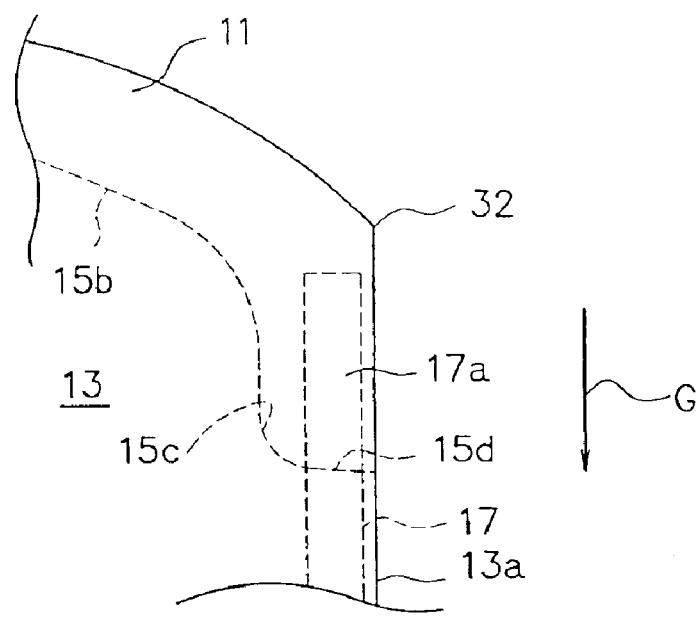
FIG. 5 is an enlarged explanatory view of the area F in FIG. 2.

In the area shown in FIG. 5, the liquid-absorbing member 12 including the tissue 15 is smaller in size than both the surface member 13 and the waterproof member 11. In other words, the surface member 13 and the waterproof member 11 are identical in size and shape, and adhered one on another.

The upper side 15b of the liquid-absorbing member 12 including the tissue 15 has approximately the same curvature as the upper edge of the surface member 13 and the waterproof member 11. The upper side 15b is connected to the area 15c curved in a direction opposite to an approximately horizontal upper edge 15d.

The edge 17a that is one of the edges of the elastic member 17 protrudes from the upper edge 15d. That is, although the upper edge 17a of the elastic member 17 protrudes from the upper edge area 15d, it is disposed inside the surface member 13 and therefor is not exposed outside. The upper edge 17a of the elastic member 17, except the bottom portion thereof, constitutes a free area not attached to the any member constituting the main body 18 of the breast pad including the surface member 13 and the waterproof member 11 by adhesive or the like. This part constitutes a free portion 17a of the elastic member 17.

With this structure, the main body can have a free portion showing the following effects without enlarging the main body.

The following effects will be obtained.

Figure 6:
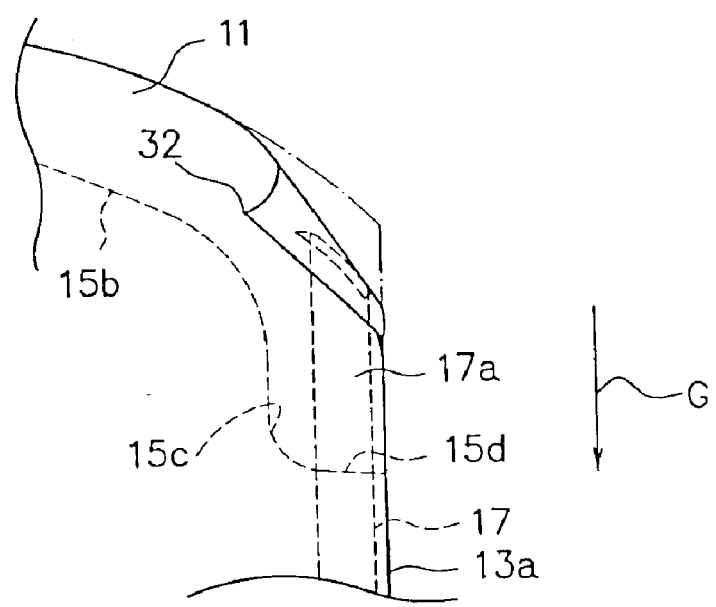
FIG. 6 is an explanatory view showing a comparative structural embodiment of the structure of FIG. 5.

As understood from FIG. 6 which is shown for the purposes of comparison, if the upper portion 17a of the elastic member 17 is fixed with means such as adhesive to the surface member 13 and/or the waterproof member 11 constituting a part of the main body 18, the elastic member 17 contracts due to the elastic function. The upper portion 17a of the elastic member 17 functions to form a dome shape, and simultaneously to pull the side upper edges of the surface member 13 and the waterproof member 11 in the direction of an arrow G.

As a result, as shown in FIG. 6, the corners 32 of the surface member 13 and the waterproof member 11 are turned inward. In other words, the corner 32 of the waterproof member 11, made of harder materials as compared to the surface member 13, faces toward a user's skin. In this manner, the corner 32 contacts a user's skin, which gives uncomfortable stimulations to the user.

On the other hand, as shown in FIG. 5, when the top 17a of the elastic member 17 constitutes a free portion, or a non-fixed portion, the above-mentioned effect will not occur at the waterproof member 11. Therefore, the corner 32 is not turned inward, and the production of uncomfortable stimulus can be avoided. Accordingly, the elastic member 17 does not produce any uncomfortable stimulation to the user while properly forming a dome-shape.

Needless to say, each elastic member 17 requires an identical or a similar structure on the respective corners of the upper and lower edges of each elastic member 17.

These free areas 17a, in a manufacturing process, are formed by disposing the extendable elastic member and then fixing the elastic member 17 to the liquid-absorbing member 12 including the tissue 15. As will be understood from the above, the edge portion 17a of the elastic member 17 is an excessive portion. Accordingly, it can be omitted since it does not contribute to the prescribed function. In this case, the area where an edge portion 17a does not exist, or the four corners of the main body 18 where the elastic member does not exist, constitutes the free portion.

If the size of the main body 18 can be made larger than the case of FIG. 2, the free area where the effect of the elastic member 17 does not reach can be formed by enlarging the area constituted only by the surface member 13 and the waterproof member 11 and forming the four corners of the liquid-absorbing member 12 including the tissue 15 to have the same configuration as that of the main body 18 without forming the curved line as mentioned above.

Figure 7:
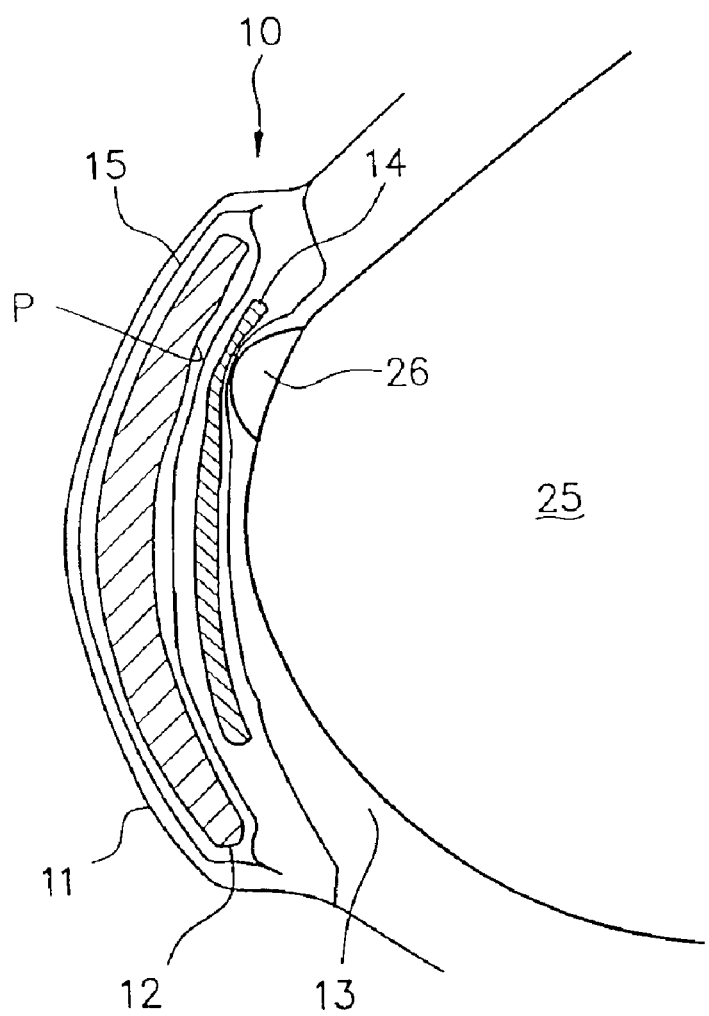
FIG. 7 is a partially enlarged cross-sectional view showing the condition of a user wearing the breast pad.
Figure 10:
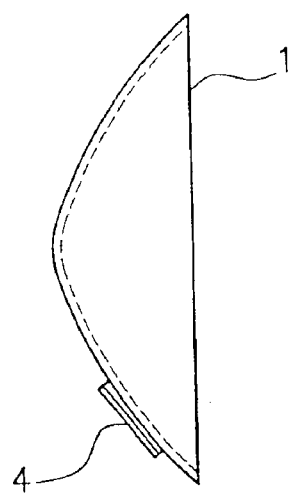
FIG. 10 is a side view of the breast pad of FIG. 5.
Figure 11:
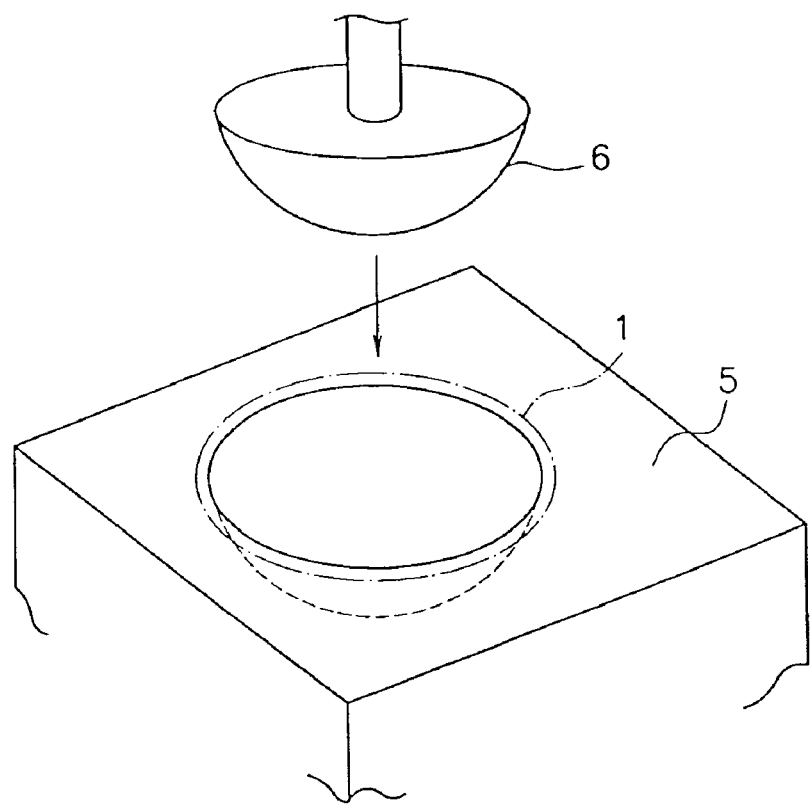
FIG. 11 is a schematic explanatory view showing the method of manufacturing the breast pad of FIG. 5.

FIG. 7 is an enlarged cross-sectional view showing a user wearing the breast pad 10. The front portion of the user's breast 25 has an approximately hemisphere-shape, such as a bowl shape, and the nipple 26 is placed near the tip thereof.

On the other hand, the breast pad 10 according to the present embodiment, as shown in the cross-sectional shape, has a dome-shape which can almost cover the user's breast 15 and can cover the nipple 26 at the concave area C due to the functions of the above-mentioned elastic members 17 and concave grooves 16.

With this structure, the breast pad 10 is not displaced from the breast 25 with time because the breast pad remains in its shape without becoming flat, nor does the dome shape deform. By means of the concave grooves 16, a three-dimensional dome shape can be formed while maintaining the dome shape more effectively as compared to the case where only elastic members 17 are provided.

Furthermore, since the main body 18 is folded along the concave grooves 16 as explained in FIG. 2, the region C protrudes outwardly, enabling the nipple 26 to be placed therein, which prevents the nipple from being unnecessarily pressed. In this manner, the nipple 26 which is sensitive during the nursing period, will not unnecessarily be stimulated and hurt.

Furthermore, since the nipple 26 can be placed softly on the surface member 16 due to the cushion member 14 and can be held in the vicinity of the region C due to the effect of the concave grooves 16 to be remained therein, the leaking of mother's milk resulting from the nipple 26 being displaced outside the effective absorbent area of the surface member 13, can be avoided.

As explained above, in the present embodiment, the side edge portion 13a of the surface member 13 is folded inwardly so as to embrace the side edge portion of the liquid-absorbing member 12 opposite to a user's skin. With this structure, since the edge of the breast pad is covered by relatively soft materials, even if this materials are placed on a user's skin, unpleasant feelings are not given to a user.

In other words, when the elastic member 17 contracts, the waterproof member 11 harder than the surface member 13 does not produce wrinkles at the circumference 18a of the main body 18 where the elastic member 17 is disposed. Wrinkles are produced by the surface member 13 made of unwoven fabric or the like. In this manner, as shown FIG. 7, in the state of wearing the breast pad, unpleasant feelings are not given to the user even if it comes in contact with the sensitive user's skin.

Furthermore, both the side edges of the main body 18 include a side edge 13a of the folded surface member 13 and an area 31 that is not adhered. In this manner, when the elastic member 17 contracts and the side edge 13a of the folded surface member 13 is pulled toward a user's skin, the edge of the waterproof member 11 will be followed and turned toward the user's skin, and does not come in contact with the user's skin. Thereby, unpleasant feelings caused by contacting the waterproof member harder than the surface member 13, can be avoided.

Furthermore, the upper edge 17*a* of the elastic member 17 is not fixed to the surface member 13 and the water member 11. Accordingly, the corner 32 does not turn inward, and the giving of unpleasant feelings to a user can be effectively avoided.

The invention is not limited to the above-mentioned embodiments.

For example, several cushion members can be placed in the main body 18.

Additionally, the concave groove 16 can be made not on the surface member 16 but, for instance, only on the liquid-absorbing member 12 mostly constituting the thickness of the main body 18. The concave groove 16 may be partially formed on a part of the materials constituting the main body 18 so long as the concave groove 16 fulfills the function for forming a bending portion.

Furthermore, the liquid-absorbing member 11, the surface member 13 and the liquid-absorbing member 12 can be made of various kinds of materials besides those of the above-mentioned embodiment.

Additionally, every member constituting the main body 18 need not necessarily be approximately round so long as the whole shape formed by laminating various different shaped members has an approximately round shape. In other words, as long as the member to which the elastic member is disposed is approximately round in shape, the member can be retained in a dome-shape.

Furthermore, some part of each constructing element of each embodiment mentioned above can be omitted, and can be voluntarily combined.

As mentioned above, the present invention can provide a breast pad which can be formed into a three-dimensional dome shape without heat treatments, and is superior in shape-retaining ability.

Furthermore, the present invention can provide a breast pad which can be formed into a dome-shape without heat treatments, and can avoid hard feelings due to thermal deformations or heat treatments.

INDUSTRIAL APPLICABILITY

Thus, the present invention can be applied as an appropriate breast pad to be placed between underwear such as a brassiere and a breast.

What is claimed is:

1. A breast pad comprising:
   a main body having a substantially round shape contacting a user's breast, the main body having an edge portion including a first edge and a second edge opposed to the first edge, the main body comprising:
   a liquid-absorbing member;
   a waterproof member provided outwardly on the liquid-absorbing member;
   a first elastic member disposed at the first edge;
   a second elastic member disposed at the second edge, and
   a pair of concave grooves provided between the first elastic member and the second elastic member, extending in an expansion direction of the first elastic member and the second elastic member.

2. The breast pad as recited in claim 1, wherein said concave grooves curve along said expansion direction of said elastic members.

3. The breast pad as recited in claim 2, wherein said concave grooves curve so as to protrude toward a central portion of said main body along said expansion direction of said elastic members.

4. The breast pad as recited in any of claims 1, 2 and 3, further comprising a surface member which comes in contact with the user's breast, said surface member being inwardly disposed on said liquid-absorbing member and a cushion member disposed between said liquid-absorbing member and said surface member.

5. The breast pad as recited in claim 4, wherein said surface member is provided with said concave grooves around a nipple-contact portion of said surface member.

6. A breast pad comprising:
   a main body having a substantially round shape, having an edge portion including a first edge and a second edge opposed to the first edge, the main body comprising:
   a surface member, wherein the surface member contacts a user's breast;
   a liquid-absorbing member having a first surface and a second surface, the first surface being provided on the surface member;
   a waterproof member provided on the second surface of the liquid-absorbing member;
   a first elastic member disposed at the first edge; and
   a second elastic member disposed at the second edge,
   wherein the surface member is extended to the second surface of the liquid-absorbing member at the edge portion.

7. The breast pad recited in claim 6, wherein said surface member is folded outwardly at the edge portion so as to embrace said liquid-absorbing member and said elastic members.

8. The breast pad recited in claim 7, wherein said elastic members are fixed between said liquid-absorbing member and said folded surface member, or between said folded surface member and said waterproof member, in a state in which said elastic members are sandwiched therebetween at the edge portion of said main body, and wherein the elastic members are not fixed to the main body at longitudinal ends thereof.

9. The breast pad recited in claim 8, wherein said liquid-absorbing member is formed to be smaller than said waterproof member and said surface member at a region in which said elastic members arc terminated, and wherein said elastic members are not fixed to the waterproof member and the surface member at the region.

10. The breast pad recited in claim 6 or 7, wherein, approximately at an expanding center of said elastic member on side edge portion of said main body, said waterproof member has an area not fixed to said liquid-absorbing member and/or said surface member.

* * * * *